US012138334B2

(12) United States Patent
Kadamkode et al.

(10) Patent No.: US 12,138,334 B2
(45) Date of Patent: *Nov. 12, 2024

(54) ANTIDANDRUFF COMPOSITION

(71) Applicant: Conopco, Inc., Englewood Cliffs, NJ (US)

(72) Inventors: Vinitha Kadamkode, Palakkad (IN); Rupak Mitra, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 342 days.

This patent is subject to a terminal disclaimer.

(21) Appl. No.: 17/631,979

(22) PCT Filed: Jul. 24, 2020

(86) PCT No.: PCT/EP2020/070904
§ 371 (c)(1),
(2) Date: Feb. 1, 2022

(87) PCT Pub. No.: WO2021/018754
PCT Pub. Date: Feb. 4, 2021

(65) Prior Publication Data
US 2022/0280401 A1 Sep. 8, 2022

(30) Foreign Application Priority Data
Aug. 1, 2019 (EP) .................................... 19189595

(51) Int. Cl.
*A61K 8/00* (2006.01)
*A61K 8/362* (2006.01)
*A61K 8/368* (2006.01)
*A61K 8/37* (2006.01)
*A61K 8/49* (2006.01)
*A61Q 5/00* (2006.01)
*A61Q 5/02* (2006.01)

(52) U.S. Cl.
CPC .............. *A61K 8/362* (2013.01); *A61K 8/368* (2013.01); *A61K 8/37* (2013.01); *A61K 8/4926* (2013.01); *A61Q 5/006* (2013.01); *A61Q 5/02* (2013.01)

(58) Field of Classification Search
CPC ....... A61K 8/362; A61K 8/368; A61K 8/4926
See application file for complete search history.

(56) References Cited

U.S. PATENT DOCUMENTS

| 3,448,132 | A | 6/1969 | Griebstein |
| 9,326,924 | B1 | 5/2016 | Fourre et al. |
| 2006/0034902 | A1* | 2/2006 | Cormier ............ A61M 37/0015 424/448 |
| 2008/0063618 | A1 | 3/2008 | Johnson et al. |
| 2011/0144151 | A1 | 6/2011 | Breen et al. |
| 2012/0101135 | A1 | 4/2012 | Klug et al. |
| 2012/0329874 | A1 | 12/2012 | Piva et al. |
| 2014/0311515 | A1 | 10/2014 | Barne et al. |
| 2014/0335029 | A1 | 11/2014 | Rudolph et al. |
| 2014/0364595 | A1* | 12/2014 | Bapat .................... A61K 8/347 544/370 |
| 2016/0000094 | A1 | 1/2016 | Modak et al. |
| 2016/0060660 | A1 | 3/2016 | Hiller et al. |
| 2017/0151165 | A1 | 6/2017 | Scheunemann et al. |
| 2017/0360663 | A1 | 12/2017 | Schulze Zur Wiesche et al. |
| 2018/0353410 | A1* | 12/2018 | Kita-Tokarczyk ....... A61K 8/65 |
| 2021/0251863 | A1 | 8/2021 | Campbell-Lee et al. |
| 2021/0283035 | A1 | 9/2021 | Cawley et al. |

FOREIGN PATENT DOCUMENTS

| BR | 102017003313 | 10/2018 |
| CN | 102480944 A | 5/2012 |
| CN | 104010525 A | 8/2014 |
| CN | 104078093 | 10/2014 |
| CN | 104152300 | 11/2014 |
| CN | 105133035 | 12/2015 |
| CN | 105296995 | 2/2016 |
| CN | 105457059 | 4/2016 |
| CN | 104116734 | 5/2016 |
| CN | 106565986 | 4/2017 |
| CN | 107519516 | 12/2017 |
| CN | 109303711 A | 2/2019 |
| CN | 109562284 A | 4/2019 |
| DE | 102017101868 | 9/2017 |
| DE | 202017001430 | 9/2017 |
| EP | 0853941 | 7/1998 |
| EP | 1082906 | 3/2001 |
| EP | 1433464 | 6/2004 |
| EP | 2181995 A2 | 5/2010 |
| EP | 2807925 | 12/2014 |
| EP | 2320860 | 10/2017 |
| FR | 2877576 | 5/2006 |

(Continued)

OTHER PUBLICATIONS

IPRP2 in PCTEP2020070905.; Jul. 8, 2021.

(Continued)

*Primary Examiner* — Necholus Ogden, Jr.
(74) *Attorney, Agent, or Firm* — Carter, DeLuca & Farrell, LLP; George Likourezos, Esq.

(57) ABSTRACT

Disclosed is an antidandruff composition comprising low amounts of piroctone olamine which synergistically interacts with benzoic acid or a salt thereof and itaconic acid or an ester thereof. The composition may be used for personal cleansing and is especially preferred to be delivered as a shampoo or hair conditioner.

14 Claims, No Drawings

(56) References Cited

FOREIGN PATENT DOCUMENTS

| | | |
|---|---|---|
| JP | 10109906 A2 | 4/1998 |
| JP | 2001226205 | 8/2001 |
| JP | 2006045127 A | 2/2006 |
| JP | 2009235315 A | 10/2009 |
| JP | 2010239872 | 10/2010 |
| JP | 2012051845 A | 3/2012 |
| JP | 2018048104 | 3/2018 |
| JP | 2021525232 A | 9/2021 |
| RU | 2642987 C2 | 1/2018 |
| WO | WO9405758 | 3/1994 |
| WO | WO9849257 | 11/1998 |
| WO | WO0061107 | 10/2000 |
| WO | WO2007084607 | 7/2007 |
| WO | WO2009019255 | 2/2009 |
| WO | WO2010018385 | 2/2010 |
| WO | WO2011092325 | 8/2011 |
| WO | 2011114151 A2 | 9/2011 |
| WO | WO2012135282 | 10/2012 |
| WO | 2014073456 A1 | 5/2014 |
| WO | WO2014161988 | 10/2014 |
| WO | WO2015197377 | 12/2015 |
| WO | WO2018092075 | 5/2018 |
| WO | 2019028506 A1 | 2/2019 |
| WO | 2019233757 A1 | 12/2019 |
| WO | 2020216757 A1 | 10/2020 |

OTHER PUBLICATIONS

Rybicki et al.; Molecular tracers preserved in Lower Jurassic "Blanowice brown coals" from southern Poland at the onset of colaification: Organic geochemical and petrological characteristes; Organic Geochemistry; 2016; pp. 77-92; 102.
4-Oxovaleric acid; Surfactant.top; Aug. 26, 2021; pp. 1-4, https://www.surfactant.top/en/saa/?type=detail&id=7524.
Anti-Dandruff (Coal Tar) Topical: Uses, Side Effects, Interactions, Pictures, Warnings and Dosing; WebMD; 2017; pp. 1-4 (URL:https://web.archive,org/web/20170802013524/https:/).
Search Report and Written Opinion in EP18175856; Jul. 6, 2018; European Patent Office (EPO).
Search Report and Written Opinion in EP18175825; Aug. 22, 2018; European Patent Office (EPO).
Search Report and Written Opinion in EP18175850; Jan. 3, 2019; European Patent Office (EPO).
Liquid Detergent for Sensitive Skin; Liquid Detergent; Nov. 1, 2015; pp. 1-3.
Fortifying Shampoo; Fortifying Shampoo; Apr. 1, 2018; pp. 1-2.
Color-Depositing Conditioner, Record Id: 5656479; Mintel GNDP; May 2018; pp. 1-3.
Search Report and Written Opinion in EP18175857; Jan. 3, 2019; European Patent Office (EPO).
Conditioner, Record ID 3951211; Mintel GNDP; Apr. 2016; pp. 1-3.
Intense repairing conditioner, Record ID 5704005; Mintel GNDP; May 2018; pp. 1-3.
Step-3 Conditioner, Record ID 4609117; Mintel GNPD; Feb. 2017; pp. 1-4.
Search report and Written Opinion in EP18175793; Jan. 8, 2019.
GNPD Mintel; GNPD Mintel; Shampoo Sunsilk Deeply; Jan. 2009; pp. 1-2 (also as XP002786946).
Advanced Repairing Shampoo; Database GNPD Mintel; 2018; pp. 1-2 (also as XP002786947).
Search Report and Written Opinion in EP18209553; May 21, 2019.
Search Report and Written Opinion in PCTEP2019062973; Jun. 25, 2019.
Search Report and Written Opinion in PCTEP2019062963; Jul. 5, 2019.
Search Report and Written Opinion in PCTEP2019062983; Jul. 8, 2019.
Search Report and Written Opinion in PCTEP2019062974; Jul. 8, 2019.
Search Report and Written Opinion in PCTEP2019062962; Aug. 2, 2019; World Intellectual Property Org. (WIPO).
Search Report and Written Opinion in EP; Aug. 29, 2019.
Search Report and Written Opinion in EP19189592; Oct. 18, 2019.
Somayeh Ghahari ; Phytochemical screening and antimicrobial activities of the constituents isolated from *Koelreuteria paniculata* leaves; Natural Product Research; Oct. 2, 2015; pp. 1865-1869; vol. 29, No. 19.
Nykaafrontendteam; Dhathri Dheedhi Anti-Dandruff for removing dandruff naturally herbal shampoo; nykaa.com; Jun. 18, 2019; 1-5.
Pan Chun-Xiu ; Investigation on the Macromolucuilar Network Structure of Xianfeng Lignite by a New Two-Step Depolymerisation; Fuel, IPC Science & Technology Press; Dec. 8, 2012; pp. 49-53; vol. 109.
Search Report and Written Opinion in EP19189595; Oct. 18, 2019.
Luan et al.; Food Fight : Role of Itaconate and Other Metabolites in Antimicrobial Defense; Cell IMetabolism; Sep. 13, 2016; pp. 379-387; vol. 24 No. 3.
Partial Search Report and Provisional Written Opinion in PCTEP2019081362; Jan. 21, 2020.
Search Report and Written Opinion in PCTEP2019081362; Mar. 16, 2020.
Search Report and Written Opinion inPCTEP2020070904; Oct. 20, 2020.
Yi Ming, "Compounds derived from immune cells treat psoriasis in mice," dated Oct. 22, 2019, pp. 1-3.
Wang Fang, "Make good use of small folk remedies, and all the pain will go away," Tianjin Science and Technology Press, dated Jan. 31, 2016, p. 35.

\* cited by examiner

ANTIDANDRUFF COMPOSITION

CROSS-REFERENCE TO RELATED PATENT APPLICATIONS

This application is a U.S. National Phase Application under 35 U.S.C. § 371 of International Application No. PCT/EP2020/070904, filed Jul. 24, 2020, which claims the benefit of priority to EP19189595.2, filed on Aug. 1, 2019, both of which are incorporated herein by reference in their entireties.

FIELD OF THE INVENTION

This invention relates to an antidandruff composition. The invention more particularly relates to a personal care or cleansing composition e.g. those to benefit hair and scalp comprising actives that interact synergistically for anti-dandruff benefits.

BACKGROUND OF THE INVENTION

The invention relates to an anti-dandruff composition useful for personal care and cleansing especially of the hair and scalp. Hair care compositions generally provide cleansing or conditioning benefits or a combination of the two. Such compositions typically comprise one or more cleansing surfactants which generally aid in cleaning the hair and/or the scalp free of undesirable soil, particles, and fatty matter.

Additionally, anti-dandruff benefit has been provided through hair care compositions. Dandruff is an issue that affects many people globally. The condition is manifested by the shedding of clumps of dead skin cells from the scalp. These are white in colour and provide an aesthetically displeasing appearance. A factor that contributes to dandruff are certain members of the Malassezia yeasts (a form of fungus). To combat these, anti-dandruff products have been developed in the form of hair cleansing shampoos. An example of a known anti-dandruff shampoo comprises sodium lauryl ether sulfate (an ethoxylated anionic surfactant) in combination with an anti-dandruff agent. Typical anti-dandruff agents used in hair care are metal pyrithione e.g zinc pyrithione (ZPTO), octopirox (piroctone olamine), azole antimicrobials (e.g. climbazole), selenium sulfide and combinations thereof. One of the issues with octopirox has been the high cost and the limited efficacy at lower concentrations.

The present inventors have been trying to solve the above problem of utilizing the efficacy of octopirox while ensuring that the cost of the product to the consumer is kept low by boosting the efficacy at low concentrations. The present inventors have been able to achieve this by combining itaconic acid or an ester thereof along with benzoic acid or a salt thereof which are found to combine synergistically with very low concentrations of octopirox for superior antifungal efficacy.

To the knowledge of the present inventors, an antimicrobial composition comprising the combination as claimed herein have not been known or published so far.

It is thus an object of the present invention to deliver higher antidandruff efficacy from very low concentrations of octopirox.

SUMMARY OF THE INVENTION

In accordance with a first aspect is disclosed an antimicrobial composition comprising itaconic acid or an ester thereof; benzoic acid or a salt thereof; and piroctone olamine.

Another aspect of the present invention relates to a method of inhibiting growth of *M. furfur* comprising applying a composition of the first aspect on to the desired skin surface.

Yet another aspect of the present invention relates to use of a composition comprising itaconic acid or an ester thereof, benzoic acid or a salt thereof; and piroctone olamine in combating dandruff.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. In other words, in specifying any ranges of values, any particular upper value can be associated with any particular lower value.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

By 'An antidandruff composition' as used herein, is meant to include a composition for topical application to skin, hair and/or scalp of mammals, especially humans to eliminate or minimize the population of fungal microorganisms thereon. It includes any product applied to a human body for also improving appearance, cleansing, odor control or general aesthetics. The composition of the present invention can be in the form of a liquid, lotion, cream, foam, scrub, gel, or bar. Non-limiting examples of such compositions include wash-off shampoos, shampoo-cum-conditioners, shower gels, hair care liquids or gels or bars. The composition of the present invention is most preferably a shampoo or a hair conditioner in the conventional lotion or semi-liquid form.

The invention relates to an antidandruff composition comprising piroctone olamine; itaconic acid or an ester thereof; and benzoic acid or a salt thereof.

Piroctone olamine or 1-Hydroxy-4-methyl-6-(2,4,4-trimethylpentyl)-2-(1H)pyridinone,2-aminoethanol salt or octopirox is a heterocyclic compound and ethanolamine salt of the hydroxamic acid derivative piroctone. It is often used in anti-dandruff shampoo as a replacement for the commonly used compound zinc pyrithione. It is a white or slightly yellow crystalline powder. It is soluble in 10% ethanol in water, soluble in solution containing surfactants in water or in 1%-10% ethanol. Piroctone olamine is an anti-dandruff active ingredient, soothes inflamed scalp and reduces flaking. It has special functions such as thickening, preservation and elimination of body offensive odour.

Piroctone olamine has the following structure:

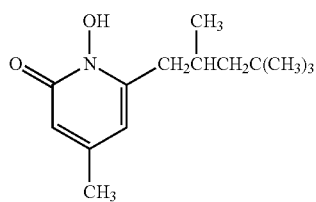

The composition preferably comprises 0.0001 to 1%, more preferably 0.0001 to 0.01%, furthermore preferably 0.0001 to 0.0006%, even more further preferably 0.0001 to 0.0003% piroctone olamine by weight of the composition.

Itaconic acid is an organic, unsaturated dicarboxylic acid. It is methacrylic acid in which one of the methyl hydrogens is substituted by a carboxylic acid group. The other names of itaconic acid are 2-methylenesuccinic or methylenebutanedioic acid. The molecular weight of itaconic acid is 130.1 g/mol. It is available as a dry white colored powder. The solubility in water is 1 g/12 ml. Itaconic acid is naturally produced by various fungi like *Aspergillus terreus, Ustilago zeae*, and *Ustilago maydis* and the yeast *Candida* sp. *Aspergillus terreus* is used for the industrial production of itaconic acid. Polymers of itaconic acid is widely used in cleaning and hygiene, energy and industry, surface coatings and agriculture. It is widely used in hair conditioning gels and in odour control products.

Itaconic acid has the following structure:

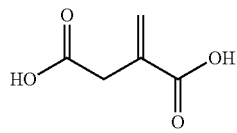

Itaconic acid esters may also be used in the composition of the invention. Suitable itaconic acid esters are dimethyl itaconate or dibutyl itaconate, preferably dimethyl itaconate.

The composition of the invention comprises benzoic acid or a salt thereof. Suitable salt of benzoic acid that may be included is sodium benzoate.

Benzoic acid is a compound comprising a benzene ring core carrying a carboxylic acid substituent. It has a role as an antimicrobial food preservative. Benzoic acid appears as a white crystalline solid. It is slightly soluble in water. Most of commercial benzoic acid is produced by the reaction of toluene with oxygen at temperatures around 200° C. in the liquid phase and in the presence of cobalt and manganese salts as catalysts. Acidic food and beverage like fruit juice (citric acid), sparkling drinks (carbon dioxide), soft drinks (phosphoric acid), pickles (vinegar) or other acidified food are preserved with benzoic acid. The structure of benzoic acid is:

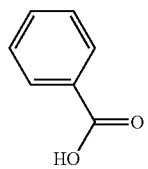

The weight ratio of itaconic acid or ester thereof to benzoic acid or a salt thereof is preferably in the range of 1:9 to 9:1.

The concentration of itaconic acid or ester thereof to enable the antidandruff efficacy is preferably in the range of 0.01 to 2%, more preferably 0.1 to 2% by weight of the composition.

It is preferred that the benzoic acid or salt thereof is included in the composition in the range of 0.01 to 2%, preferably 0.1 to 2% by weight of the composition. Preferably the total amount of itaconic acid or an ester thereof and benzoic acid or salt thereof is included in the composition in the range of 0.15 to 3%, preferably 0.2 to 2% by weight of the composition.

It is preferred that the weight ratio of piroctone olamine to itaconic acid or ester thereof is in the range of 1:10 to 1:250.

It is preferred that the weight ratio of piroctone olamine to benzoic acid or salt thereof is in the range of 1:10 to 1:250.

The composition of the invention preferably additionally comprises a cosmetically acceptable carrier. The carrier is preferably chosen such that the composition of the invention can be delivered for use as a personal cleansing composition. As per one aspect the cosmetically acceptable carrier is water or an aqueous solution. According to another preferred aspect, the carrier additionally comprises a surfactant. The cosmetically acceptable vehicle is such that the composition can be prepared as a shampoo, conditioner, body wash, hand wash or face wash product, cream, lotion, gel, powder, ointment, or a soap bar.

According to a further preferred aspect of the present invention, the composition is either a shampoo, a hair conditioner, or a body wash product, most preferably a shampoo or a hair conditioner composition. When so formulated, the composition additionally comprises a cosmetically acceptable carrier selected from an anionic, cationic or amphoteric or zwitterionic surfactant.

As per an especially preferred aspect of the invention, the composition is a shampoo. The composition of the invention especially shampoos are formulated with an anionic surfactant e.g. an alkyl sulphate and/or ethoxylated alkyl sulfate surfactant. These anionic surfactants are preferably present at a level of from 1 to 20%, preferably 2 to 16%, furthermore preferably from 3 to 16% by weight of the composition. Preferred alkyl sulfates are C8-18 alky sulfates, more preferably C12-18 alkyl sulfates, preferably in the form of a salt with a solubilising cation such as sodium, potassium, ammonium or substituted ammonium.

Preferred alkyl ether sulfates are those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES). SLES having an average degree of ethoxylation of from 0.5 to 3, preferably 1 to 3 is especially preferred.

Shampoo compositions according to the invention may comprise one or more further anionic cleansing surfactants which are cosmetically acceptable and suitable for topical application to the hair.

A composition of the invention preferably additionally comprises an amphoteric surfactant preferably a betaine surfactant preferably an alkyl amidopropyl betaine surfactant for example cocamidopropyl betaine. In a preferred embodiment, the composition comprises from 0.1 to 10 wt. %, preferably from 0.5 to 8 wt. %, more preferably from 1 to 5 wt. % of a betaine surfactant.

To enhance deposition of actives from compositions of the invention especially shampoos, cationic polymers are generally included therein. In the present invention too, it is preferred that the composition additionally includes 0.01 to 2.0% of a cationic polymer. The cationic polymer is preferably guar hydroxypropyl trimonium chloride. Guar polymer predominantly contains galactomannan polymer chains. This polymer is available at various molecular weights and degree of cationic substitutions depending on how much the guar has been hydrolysed and cationised. The cationic polymer is preferably present in 0.04 to 0.5%, more preferably 0.08 to 0.25% by weight of the composition.

The pH of the composition is preferably equal to or higher than 4.0, more preferably in the range of 5.0 to 10.0.

Preferably the composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives.

Suspending agent, if included, will generally be present in a shampoo composition of the invention at levels of from 0.1 to 10%, preferably from 0.5 to 6%, more preferably from 0.5 to 4% by total weight of suspending agent based on the total weight of the composition.

A composition of the invention may contain other ingredients for enhancing performance and/or consumer acceptability. Such ingredients include fragrance, dyes and pigments, pH adjusting agents, pearlescers or opacifiers, viscosity modifiers, preservatives, and natural hair nutrients such as botanicals, fruit extracts, sugar derivatives and amino acids.

The composition of the invention is preferably aqueous based. It preferably comprises high amounts of water preferably from 70 to 95% by weight of the composition.

When conditioning benefits are to be delivered through the composition of the invention the composition is called a hair conditioner. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. An especially useful conditioning agent is a silicone compound, preferably a non-volatile silicone compound. Advantageously compositions herein may include one or more silicones. The silicones are conditioning agents found in dispersed or suspended particulate form. They are intended to deposit onto hair remaining behind after rinsing of the hair with water. Suitable silicone oils may include polyalkyl siloxanes, polyaryl siloxanes, polyalkylaryl siloxanes, polyether siloxane copolymers and mixtures thereof. Amino silicones are often formulated with shampoo compositions. Amino silicones are silicones containing at least one primary amine, secondary amine, tertiary amine or a quaternary ammonium group. High molecular weight silicone gums can also be utilized. Another useful type are the crosslinked silicone elastomers such as Dimethicone/Vinyl/Dimethicone Crosspolymers (e.g. Dow Corning 9040 and 9041).

Amounts of the silicone in compositions where present may range from about 0.1 to about 10 wt. %, preferably from about 0.1 to about 8 wt. %, more preferably from about 0.3 to about 5 wt. % by weight of the hair care compositions.

The pH of the composition is preferably equal to or higher than 4.0, more preferably in the range of 5.0 to 7.0.

The hair conditioning composition usually comprises conditioning surfactants selected from cationic surfactants, used singly or in admixture. Suitable cationic surfactants for use in conditioner compositions according to the invention include: cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof.

The most preferred cationic surfactants for use in the composition are stearamidopropyl dimethylamine, behentrimonium chloride, or stearyl trimethyl ammonium chloride. In conditioners of the invention, the level of cationic surfactant will generally range from 0.1% to 5%, preferably 0.5 to 2.5% by weight of the composition.

Hair conditioning compositions of the invention preferably may also additionally comprise a fatty alcohol. The combined use of fatty alcohols and cationic surfactants in conditioning compositions is believed to be especially advantageous, because this leads to the formation of a lamellar phase, in which the cationic surfactant is dispersed.

The level of fatty alcohol in conditioners of the invention will generally range from 0.5 to 10%, preferably from 0.1% to 8%, more preferably from 0.2% to 7%, most preferably from 0.3% to 6% by weight of the composition. The weight ratio of cationic surfactant to fatty alcohol is suitably from 1:1 to 1:10, more preferably from 1:1.5 to 1:8, optimally from 1:2 to 1:5.

The composition of the invention may be used for skin care e.g. body, hand or face wash. The antimicrobial composition may further comprise a surfactant. The preferred surfactants are nonionic surfactants, such as $C_8$-$C_{22}$, preferably $C_8$-$C_{16}$ fatty alcohol ethoxylates, comprising between 1 and 8 ethylene oxide groups when the product is in the liquid form. The surfactants are preferably selected from primary alkyl sulphate, secondary alkyl sulphonates, alkyl benzene sulphonates, or ethoxylated alkyl sulphates. The composition may further comprise an anionic surfactant, such as alkyl ether sulphate preferably those having between 1 and 3 ethylene oxide groups, either from natural or synthetic source and/or sulphonic acid. Especially preferred are sodium lauryl ether sulphates. Alkyl polyglucoside may also be present in the composition, preferably those having a carbon chain length between C6 and C16.

Thus, in a highly preferred aspect, the antimicrobial compositions include the surfactant selected from the group of anionic surfactant, fatty acid amide, alkyl sulphate, linear alkyl benzene sulphonate, and combinations thereof.

When the surfactants are present, the antimicrobial composition preferably comprises 1 to 90% surfactant by weight of the composition.

When surfactant is used, a particularly preferred surfactant is soap. Soap is a suitable surfactant for personal washing applications of the antimicrobial composition of the invention. The soap is preferably $C_8$-$C_{24}$ soap, more preferably $C_{10}$-$C_{20}$ soap and most preferably $C_{12}$-$C_{18}$ soap. The cation of the soap can be alkali metal, alkaline earth metal or ammonium. Preferably, the cation of the soap is selected from sodium, potassium or ammonium. More preferably the cation of the soap is sodium or potassium.

A typical fatty acid blend consisted of 5 to 30% coconut fatty acids and 70 to 95% fatty acids by weight of soap. Fatty acids derived from other suitable oils/fats such as groundnut, soybean, tallow, palm, palm kernel, etc. may also be used in other desired proportions.

When present, the soap, of the present is preferably present in an amount of 1 to 90%, preferably from 10 to 85%, more preferably 25 to 75% by weight of the composition. Preferred compositions may include other known ingredients such as perfumes, pigments, preservatives, emollients, sunscreens, emulsifiers, gelling agents and thickening agents. Choice of these ingredients will largely depend on the format of the composition.

Water is a preferred carrier. When water is present, it is preferably present in at least 1%, more preferably at least 2%, furthermore preferably at least 5% by weight of the composition. When water is the carrier, a preferred liquid composition comprises 10 to 99.8% by weight water.

Also disclosed in accordance with this invention is non-therapeutic use of the composition for delivering anti-dandruff benefits. The following non-limiting examples further illustrate preferred embodiments of the invention. All percentages referred to in the examples and throughout this specification are based on total weight unless otherwise indicated.

EXAMPLES

Examples 1-15: Antifunqal Efficacy of Compositions as Per the Invention

The samples as given in Table 1 were subjected to their anti fungal efficacy on M. furfur as described hereinafter.

Antifunqal Activity:

The test organism used in the assay is *Malassezia furfur* 14521. The *M. furfur* were revived from glycerol stock in YPD agar plates (yeast extract peptone dextrose media) containing 1% corn oil. The composition of YPD is yeast extract:10 g/litre, dextrose 20 g/litre, Peptone 20 g/litre and agarose 0.15%. The plates were incubated at 30° C. for 72 hours for forming fungal colonies. A suspension culture of *M. furfur* was made using the colonies from plates in YPD broth. The optical density of the suspension culture was adjusted to 0.6 using spectrophotometer. This suspension was diluted in the ratio of 1:10 using YPD broth and 100 µl of this culture was added into each well of 96 well test plate. A stock solution of 40× strength of piroctone olamine was prepared for each of the concentrations tested eg for 0.0.001% test concentration of piroctone olamine a stock of 0.04% was prepared in DMSO (dimethyl sulphoxide). 5 µl of piroctone olamine was added to 100 µl of *M. furfur* culture. A stock solution of 4× strength of itaconic acid or sodium benzoate was prepared for each of the concentrations tested e.g. for 0.0.001% test concentration of itaconic acid or sodium benzote a stock of 0.004% was prepared in YPD broth. 50 µl of itaconic acid or sodium benzoate was added to 100 µl of *M. furfur* culture. In wells containing only one test ingredient, (itaconic acid or sodium benzoate only) 50 µl of test ingredient was added to 100 µl of fungal culture and then made up the volume to 200 µl with YPD broth. In wells containing only piroctone olamine 5 µl of piroctone olamine was added to 100 µl of fungal culture and then made up the volume to 200 µl with YPD broth. The plates were incubated at 30° C. for 72 hours. Post incubation 10 µl of 1% resazurin was added to each well and incubated for 18 hours at 30° C. Resazurin (7-Hydroxy-3H-phenoxazin-3-one 10-oxide) is a blue dye which is used as an oxidation reduction indicator in cell viability assays. The dehydrogenase enzymes in live cells reduce Resazurin (blue and non-fluorescent) to form the red fluorescent dye resorufin. The wells containing viable cells appear in pink color and the wells with dead cells appear blue/purple. The anti-fungal efficacy of the ingredient or combination of ingredients is calculated based on the colour development.

Evaluation of synergy using fractional inhibitory concentration (ΣFIC).

The combinations of test ingredients with synergistic anti-fungal benefits were evaluated using ΣFIC method. The ΣFIC of the combinations were calculated using the following formula:

ΣFIC of combination A+B+C=[Concentration of A]/MIC of A+[concentration of B]/MIC of B+[Concentration of C]/MIC of C, where MIC is the Minimum inhibitory concentration (MIC) of ingredient. MIC of a test ingredient is the lowest concentration of the ingredient required to inhibit the growth of the test organism.

The MIC of the various active used were determined to be as given below:
Dimethyl itaconate: 0.5 wt %
Sodium benzoate: 0.5 wt %
Piroctone olamine: 0.002 wt %

The ΣFIC values for the various combinations are given in Table 1 below:

TABLE 1

| Example | Itaconic acid (wt %) | Sodium benzoate (wt %) | Piroctone olamine (wt %) | ΣFIC |
|---|---|---|---|---|
| 1 | 0.06 | 0.03 | 0.00025 | 0.425 |
| 2 | 0.125 | 0.03 | 0.00025 | 0.685 |
| 3 | 0.06 | 0.06 | 0.00025 | 0.485 |
| 4 | 0.125 | 0.06 | 0.00025 | 0.745 |
| 5 | 0.03 | 0.125 | 0.00025 | 0.495 |
| 6 | 0.03 | 0.03 | 0.0005 | 0.43 |
| 7 | 0.06 | 0.03 | 0.0005 | 0.55 |
| 8 | 0.125 | 0.03 | 0.0005 | 0.81 |
| 9 | 0.03 | 0.06 | 0.0005 | 0.49 |
| 10 | 0.06 | 0.06 | 0.0005 | 0.61 |
| 11 | 0.03 | 0.03 | 0.001 | 0.68 |
| 12 | 0.06 | 0.03 | 0.001 | 0.08 |
| 13 | 0.125 | 0.03 | 0.001 | 1.06 |
| 14 | 0.03 | 0.06 | 0.001 | 0.74 |
| 15 | 0.06 | 0.06 | 0.001 | 0.86 |

The data in Table 1 above indicates that a combination of itaconic acid, sodium benzoate and piroctone olamine at very low concentration gives synergistic antifungal activity.

Examples 16-25: Antifungal Efficacy of Compositions as Per the Invention Using Ester of Itaconic Acid The samples as given in Table 1 were subjected to their anti fungal efficacy on *M. furfur* as described hereinbefore.

The ΣFIC values for the various combinations are given in Table 2 below:

TABLE 2

| Example | Dimethyl Itaconate (wt %) | Sodium benzoate (wt %) | Piroctone olamine (wt %) | ΣFIC |
|---|---|---|---|---|
| 16 | 0.03 | 0.03 | 0.00025 | 0.245 |
| 17 | 0.06 | 0.03 | 0.00025 | 0.305 |
| 18 | 0.125 | 0.03 | 0.00025 | 0.435 |
| 19 | 0.25 | 0.03 | 0.00025 | 0.685 |
| 20 | 0.03 | 0.06 | 0.00025 | 0.305 |
| 21 | 0.015 | 0.03 | 0.0005 | 0.34 |
| 22 | 0.03 | 0.03 | 0.0005 | 0.37 |
| 23 | 0.06 | 0.03 | 0.0005 | 0.43 |
| 24 | 0.125 | 0.03 | 0.0005 | 0.56 |
| 25 | 0.25 | 0.03 | 0.0005 | 0.81 |

The data in Table 2 indicates that similar data is obtained when dimethyl itaconate is used instead of itaconic acid.

The invention claimed is:

1. An antimicrobial composition comprising itaconic acid or an ester thereof; benzoic acid or a salt thereof; and piroctone olamine.

2. The composition as claimed in claim 1 wherein the ester of itaconic acid is dimethyl itaconate.

3. The composition as claimed in claim 1 wherein the salt of benzoic acid is sodium benzoate.

4. The composition as claimed in claim 1, wherein the concentration of itaconic acid or the ester thereof is in the range of 0.01 to 2% by weight of the composition.

5. The composition as claimed in claim 1, wherein the concentration of benzoic acid or the salt thereof is in the range of 0.01 to 2% by weight of the composition.

6. The composition as claimed in claim 1, wherein the concentration of piroctone olamine is from 0.0001 to 1.

7. The composition as claimed in claim 1, wherein the weight ratio of piroctone olamine to itaconic acid or the ester thereof is in the range of 1:10 to 1:250.

8. The composition as claimed in claim 1, wherein the weight ratio of piroctone olamine to benzoic acid or the salt thereof is in the range of 1:10 to 1:250.

9. The composition as claimed in claim 1, wherein the composition is a shampoo or a hair conditioner.

10. The composition as claimed in claim 1, additionally comprising a cosmetically acceptable carrier selected from an anionic surfactant, a cationic surfactant, an amphoteric surfactant, or a zwitterionic surfactant.

11. A method of inhibiting growth of *M furfur* comprising applying the composition as claimed in claim 1 on a desired skin surface.

12. A method of combating dandruff comprising applying a composition comprising itaconic acid or an ester thereof; benzoic acid or a salt thereof; and piroctone olamine.

13. The composition as claimed in claim 6, wherein the concentration of piroctone olamine is from 0.0001 to 0.0006% by weight of the composition.

14. The composition as claimed in claim 13, wherein the concentration of piroctone olamine is from 0.0001 to 0.0003% by weight of the composition.

* * * * *